(12) United States Patent
Eriksson et al.

(10) Patent No.: US 8,298,197 B2
(45) Date of Patent: Oct. 30, 2012

(54) WOUND CHAMBER FOR LIMB

(76) Inventors: Elof Eriksson, Wellesley Hills, MA (US); W. Robert Allison, Sudbury, MA (US); Christian Baker, Weymouth, MA (US)

( * ) Notice: Subject to any disclaimer, the term of this patent is extended or adjusted under 35 U.S.C. 154(b) by 520 days.

(21) Appl. No.: 11/994,168

(22) PCT Filed: Jun. 29, 2006

(86) PCT No.: PCT/US2006/025391
§ 371 (c)(1),
(2), (4) Date: Jul. 10, 2008

(87) PCT Pub. No.: WO2007/002835
PCT Pub. Date: Jan. 4, 2007

(65) Prior Publication Data
US 2009/0124987 A1    May 14, 2009

Related U.S. Application Data

(60) Provisional application No. 60/694,849, filed on Jun. 29, 2005.

(51) Int. Cl.
*A61M 35/00* (2006.01)
(52) U.S. Cl. .......... 604/289; 604/292; 604/293
(58) Field of Classification Search .......... 604/289, 604/290, 292, 293, 304–306; 606/202; 602/3
See application file for complete search history.

(56) References Cited

U.S. PATENT DOCUMENTS

| | | | |
|---|---|---|---|
| 4,003,371 A * | 1/1977 | Fischer | 604/23 |
| 4,772,259 A * | 9/1988 | Frech et al. | 604/23 |
| 5,312,385 A * | 5/1994 | Greco | 604/356 |
| 5,437,602 A | 8/1995 | Polyakov et al. | |
| 5,437,651 A | 8/1995 | Todd et al. | |
| 5,447,504 A * | 9/1995 | Baker et al. | 604/289 |
| 5,527,265 A | 6/1996 | McKeel | |
| 5,592,953 A * | 1/1997 | Delao | 128/882 |
| 5,720,713 A | 2/1998 | Hutchison | |
| 5,807,290 A | 9/1998 | Barry | |
| 6,053,882 A | 4/2000 | Johansen | |
| 6,083,209 A * | 7/2000 | Marasco, Jr. | 604/290 |
| 6,290,685 B1 | 9/2001 | Insley et al. | |

(Continued)

FOREIGN PATENT DOCUMENTS

| | | |
|---|---|---|
| GB | 2378392 A | 12/2003 |
| JP | 51-22888 | 2/1976 |

OTHER PUBLICATIONS

International Search Report and Written Opinion for Int'l Application No. PCT/US06/25391, Feb. 2, 2007.

(Continued)

*Primary Examiner* — Lynne Anderson
(74) *Attorney, Agent, or Firm* — Quarles & Brady LLP (57) ABSTRACT

A wound dressing includes a chamber (12) defining a treatment space (14) and at least one opening (20) communicating with the treatment space. In one embodiment, a plurality of channels are defined on an inner wall of the chamber. In another embodiment, a tube (31) extends through the chamber and into the treatment space and defines a plurality of openings (35) in a portion of the tube extending into the treatment space. In yet another embodiment, a tube extends through the chamber and into the treatment space and comprises a plurality of branches (37) extending to different regions of the treatment space.

16 Claims, 6 Drawing Sheets

U.S. PATENT DOCUMENTS

| | | | |
|---|---|---|---|
| 6,652,484 B1 | 11/2003 | Hunckler et al. | |
| 7,540,283 B2 * | 6/2009 | Loori et al. | 128/202.12 |
| 2005/0137539 A1 | 6/2005 | Biggie et al. | |
| 2006/0293630 A1 * | 12/2006 | Manna et al. | 604/327 |
| 2008/0108977 A1 | 5/2008 | Heaton et al. | |

OTHER PUBLICATIONS

U.S. Patent and Trademark Office; Non-Final Office Action for U.S. Appl. No. 12/601,394; dated Jul. 2, 2012; 31 pages.

* cited by examiner

FIG. 21 ated Jun. 29, 2005, incorporated herein by reference as if set forth in its entirety.
WOUND CHAMBER FOR LIMB

CROSS-REFERENCE TO RELATED APPLICATIONS

This application claims the benefit of U.S. Provisional Patent Application No. 60/694,849, filed Jun. 29, 2005, incorporated herein by reference as if set forth in its entirety.

STATEMENT REGARDING FEDERALLY SPONSORED RESEARCH OR DEVELOPMENT

Not applicable.

BACKGROUND OF THE INVENTION

The invention relates generally to the field of wound treatment, and more particularly to a wound chamber for treating wounds on a limb of the body.

Various techniques are employed to treat open wounds. In some cases, open wounds may be treated with moist or dry gauze. However, such treatment may result in excessive pain, dehydration of the wound, loss of fluids and proteins, loss of heat or delayed healing. To delay the appearance of infection, burn wounds may be additionally treated with antibacterial creams and the like.

Open wounds appear to heal faster in an environment that is somewhere between moist and dry. Partial thickness wounds heal faster when covered with a polyethylene film than when exposed to air. Conventionally, dressings with some water permeability provide the optimal conditions for healing.

Wound chambers for protecting open wounds and providing environmental control of the treatment site have been developed. For example, an exemplary wound chambers and methods for use are described in U.S. Pat. No. 5,152,757, entitled "System for Diagnosis and Treatment of Wounds," by Elof Eriksson, and U.S. patent application Ser. No. 11/130,490, entitled "Wound Chamber With Remote Access Portal," by Eriksson et al., each of which is incorporated herein by reference as if set forth in its entirety.

A wound chamber typically includes a chamber for enclosing a predetermined surface area about a wound on a patient. The wound chamber is sealed to the skin immediately adjacent to the wound. However, certain wounds on and around a limb may not be treatable by a wound chamber that is intended for use on relatively flat skin surfaces. Instead, it may be necessary to enclose all or a portion of a limb in a chamber in order to create a chamber environment around the wound. In addition to other features, the wound chamber may have a portal for introducing treatment fluid and treatment additives into the wound chamber and extracting wound fluid and/or air from the wound chamber. Such operations are typically performed using a syringe or similar delivery/extraction device. For example, the portal may be an injection portal made of a self-sealing material through which a hollow steel needle can be passed. The use of a steel needle in close proximity to the patient creates a risk of injury to the patient and also to the health care provider. An additional risk of the needle damaging the wound chamber is also present. In some clinical applications, the wound chamber itself may be covered by a secondary dressing or covering, such as gauze or an elastic bandage. In such circumstances, a portal located directly on the chamber would be covered by the secondary dressing and would be inaccessible.

The present invention is directed to providing a chamber to treat wounds on limbs, and to overcoming, or at least reducing the effects of, one or more of the problems set forth above.

BRIEF SUMMARY OF THE INVENTION

A wound dressing includes a chamber defining a treatment space and at least one opening communicating with the treatment space.

In aspect of the invention a plurality of channels are defined on an inner wall of the chamber.

In another aspect of the invention, a tube extends through the chamber and into the treatment space and defines a plurality of openings in a portion of the tube extending into the treatment space.

In yet another aspect of the invention, a tube extends through the chamber and into the treatment space and comprises a plurality of branches extending to different regions of the treatment space.

BRIEF DESCRIPTION OF THE SEVERAL VIEWS OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

While the present invention may be embodied in any of several different forms, the present invention is described herewith the understanding that the present disclosure is to be considered as setting forth an exemplification of the present invention that is not intended to limit the invention to the specific embodiment(s) illustrated. Nothing in this application is considered critical or essential to the present invention unless explicitly indicated as being "critical" or "essential."

Figure 1:
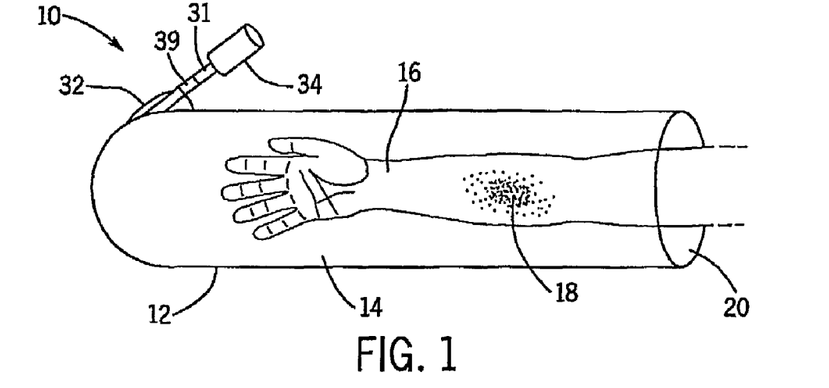
FIG. 1 is perspective view of a limb dressing in accordance with one embodiment of the present invention.

Referring first to FIG. 1, a sectional view of a limb dressing 10 is provided. The limb dressing 10 includes a chamber 12 defining a treatment space 14. A limb 16 with a wound 18 is shown within the treatment space 14. The limb dressing 10 includes an opening 20 that communicates with the treatment space 14 and may be sealed about the limb 16 of a patient so that the wound 18 to be treated is enclosed within the treatment space 14.

Figure 2:
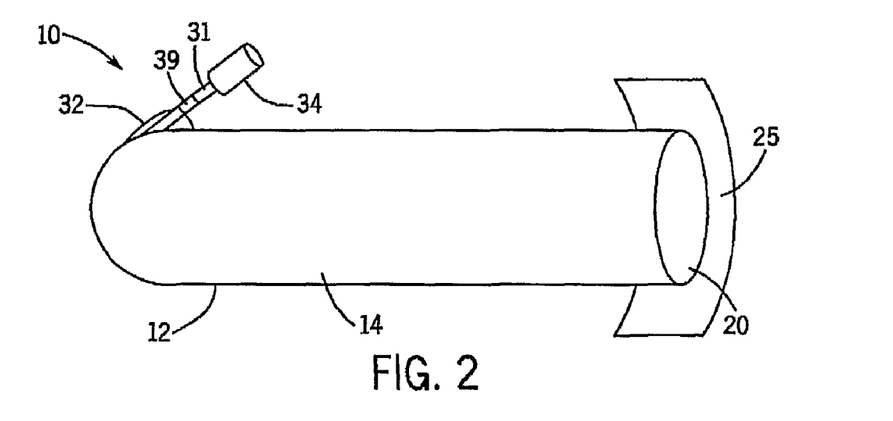
FIG. 2 is a perspective view of the limb dressing with an attached strip of adhesive backed tape.
Figure 3:
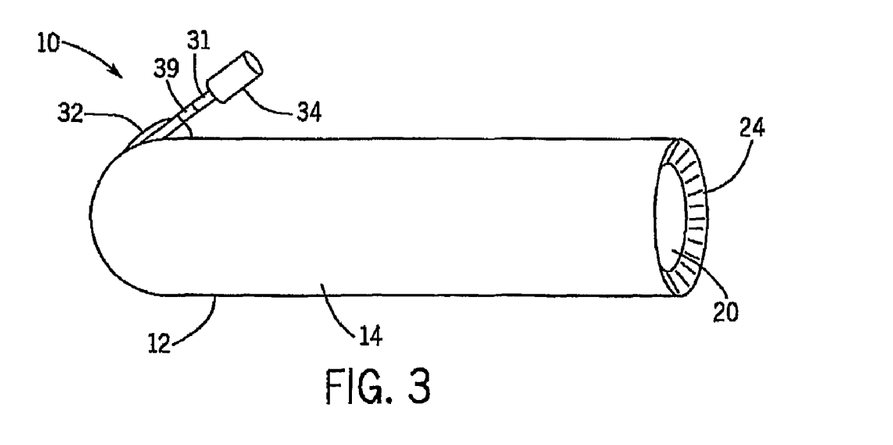
FIG. 3 is a perspective view of the limb dressing with an internal adhesive surface closure.
Figure 4:
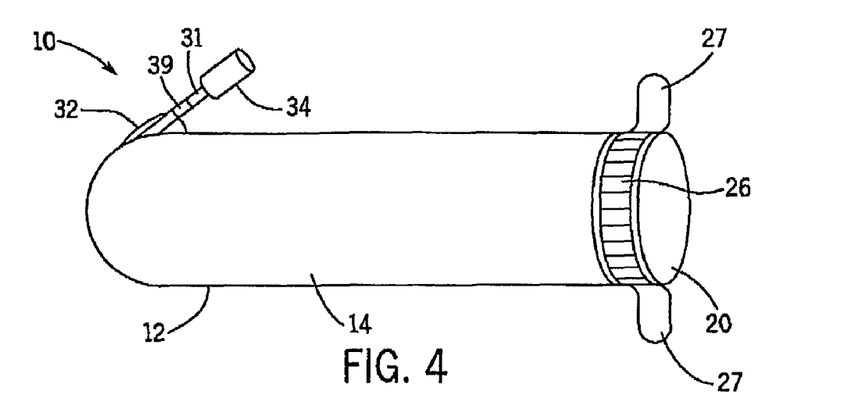
FIG. 4 is a perspective view of the limb dressing with a cuff and drawstring closure.
Figure 5:
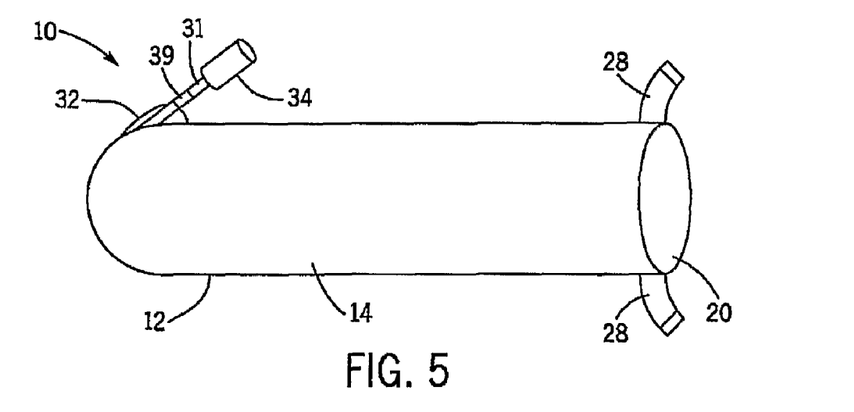
FIG. 5 is a perspective view of the limb dressing with a closing strap.

Referring next to FIGS. 2-5, various techniques may be used to secure the limb dressing 10 to the limb 16. In the embodiment of FIG. 2, the opening 20 has no integrated system for sealing. Adhesive tape 25 may be applied by a user employing the limb dressing 10. In the embodiment of FIG. 3, an adhesive material 24 is provided on the inside of the chamber wall near the opening 20. FIG. 4 shows a cuff 26 and cooperating drawstring 27. FIG. 5 shows connecting straps 28.

Figure 6:
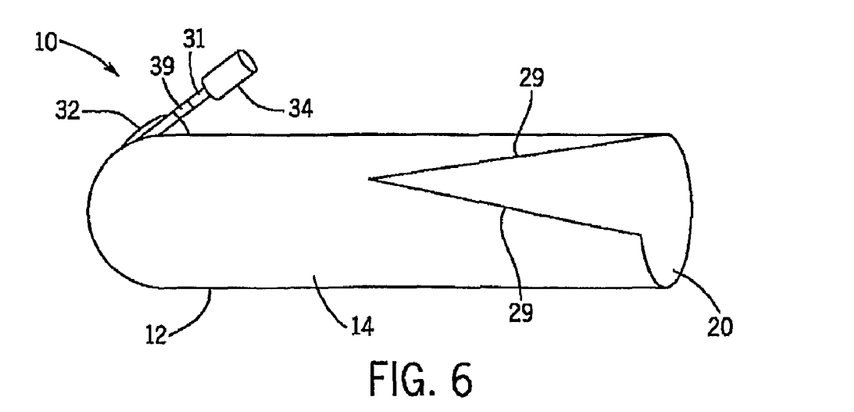
FIG. 6 is a perspective view of the limb dressing with a seam that may be opened and resealed.

Turning to FIG. 6 a seam 29 may be opened to facilitate the installation of the chamber 12 around the limb 16. The seam 29 may be unsealed and resealed by numerous methods known to those of ordinary skill in the art, such as with an adhesive tape. The seam 29 allows the limb dressing 10 to be applied in a manner that reduces the likelihood of contact between the chamber 12 and the wound 18 as the limb 16 is passed through the opening 20.

Figure 7:
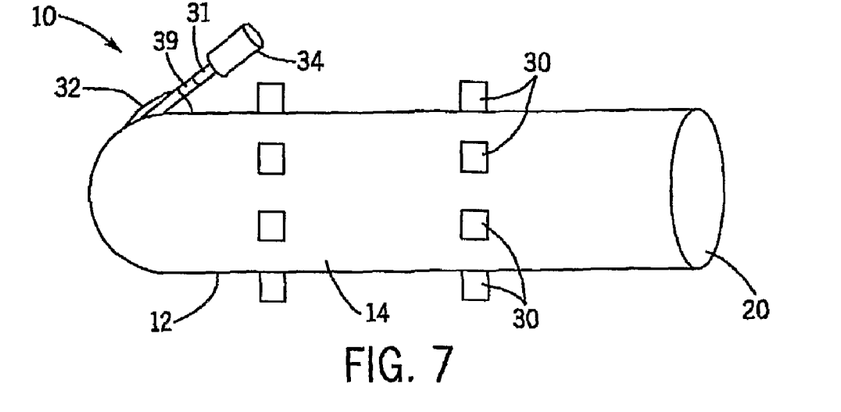
FIG. 7 is a perspective view of the limb dressing with straps for gathering and retaining loose portions of the dressing.

As shown in FIG. 7, tabs 30 may be used to reduce the cross-sectional area of the chamber 21 to gather the chamber 12 around the limb after the chamber has been installed. The tabs 30 may be used to gather any loose material around the limb after the chamber has been installed. The tabs 30 may be constructed of Velcro® or other self-sticking material. The tabs 30 may also be simple drawstrings that are tied to one another. In general, the tabs 30 can be joined to one another to gather any loose material of the chamber 12, particularly in the case of a patient with a small limb 16.

Returning to FIG. 1, a tube 31 is attached to the chamber 12 and communicates with the treatment space 14. The tube 31 may be permanently fixed to the chamber 12, or a fitting 39 may be provided to allow removal of the tube 31. The tube 31 is constructed so that it will maintain its shape, and will not collapse. A distal end of the tube 31 terminates in a portal 34. In one embodiment, the portal 34 may be a female Luer fitting. As used herein the terms portal and fitting may be used interchangeably, depending on the particular implementation. A fitting generally refers to a device that mates with a complementary, interfacing device, while a portal may relate to a device into which something is inserted, such as a needle. The tube 31 is sealed to the chamber 12 in such a manner as to prevent the escape of liquid or air from the treatment space 14. The juncture of the tube 31 and the chamber 12 may be reinforced with a flange 32. Although only one tube 31 and portal 34 are illustrated, the invention is not so limited, and multiple tubes 31 and associated portals 34 may be provided for accessing the treatment space 14. One tube 31 and portal 34 may be used as an inlet for providing treatment substances to the treatment space 14, while another tube 31 and portal 34 may be used as an outlet for removing substances from the treatment space 14. Such an inlet and outlet arrangement may be useful for administering a continuous treatment stream.

Figure 8:
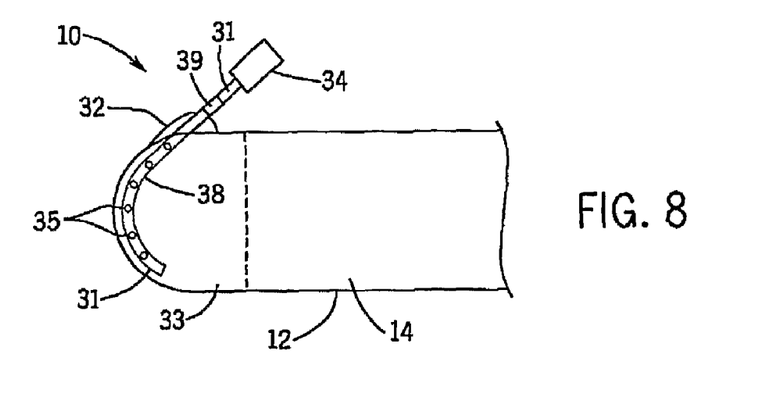
FIG. 8 is a sectional view of a tube extending into the treatment space of a wound chamber in the limb dressing.
Figure 9:
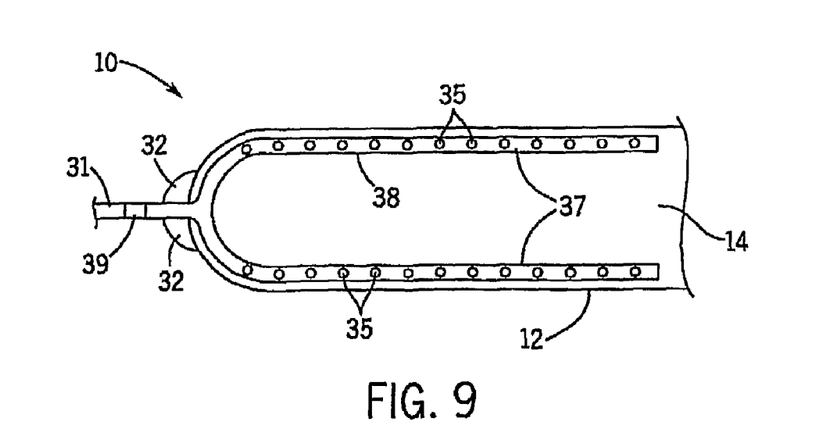
FIGS. 9 and 10 are sectional views of a branched tube extending into the treatment space.
Figure 10:
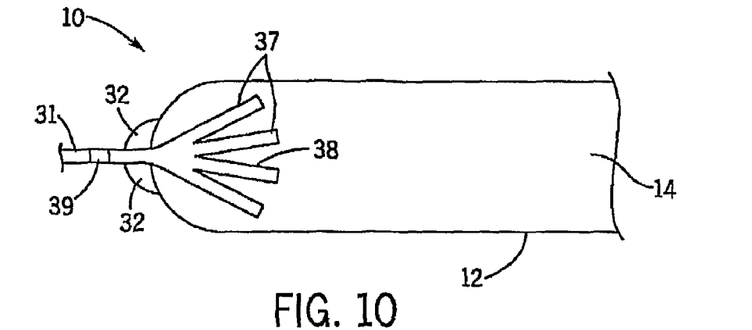

The tube 31 may terminate at a wall of the chamber 12, or it may extend through the wall a distance and terminate within the treatment space 14 as shown in FIGS. 8-10. The composition of the chamber 12 may be strengthened in area 33 as shown in FIG. 8 by increasing the thickness of the walls of chamber 12 to provide further protection for the portion 38 of the tube 31 within treatment space 14.

As seen in FIGS. 8 and 9, the portion 38 of the tube 31 within the treatment space 14 may be perforated with one or more holes 35 to facilitate the flow of liquid or air through the tube 31. The tube 31 may extend further into treatment space 14 in branches 37 as shown in FIGS. 9 and 10.

Figure 11:
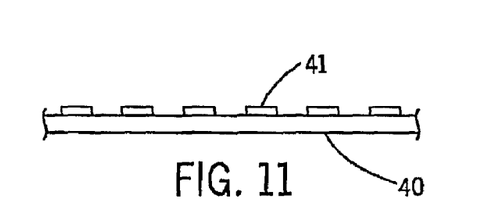
FIG. 11 is a sectional view of the wall of a wound chamber with raised ridges defined in the interior side of such wall.
Figure 12:
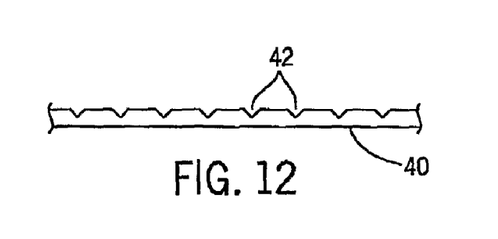
FIG. 12 is a sectional view of the wall of a wound chamber with grooves defined in the interior side of such wall.
Figure 13:
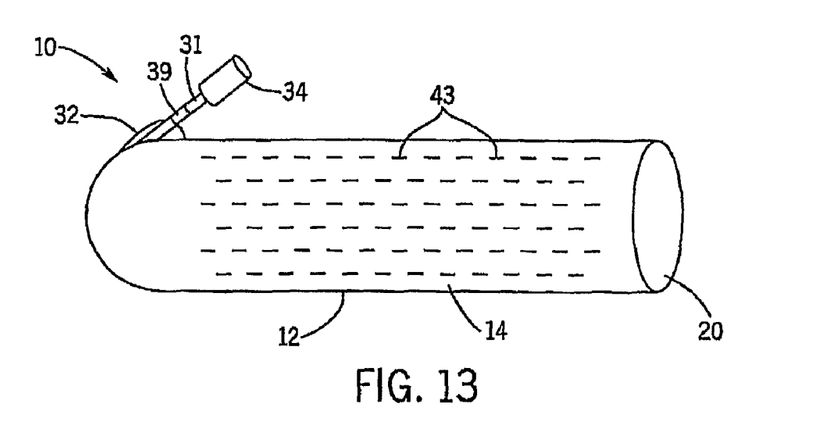
FIGS. 13-16 are perspective views of the limb dressing with varying channel patterns defined in the interior walls of the chamber.
Figure 14:
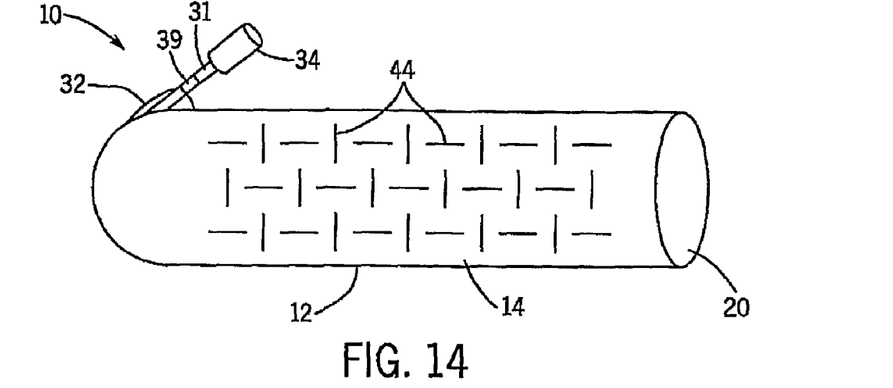
Figure 15:
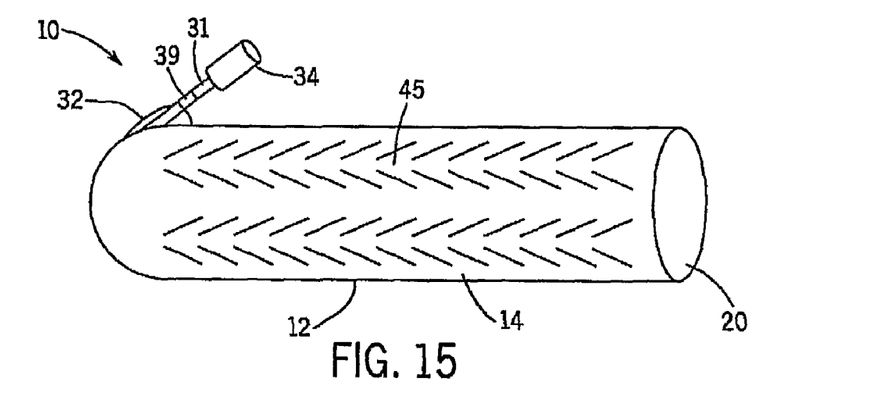
Figure 16:
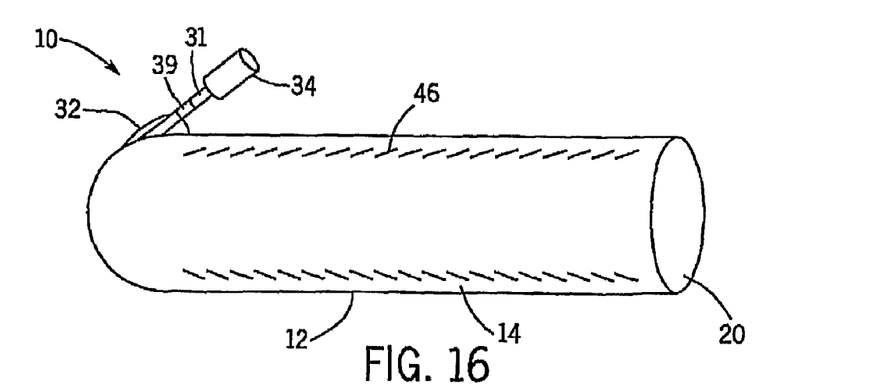

Turning to FIGS. 11-16, walls 40 of chamber 12 may be configured on the interior side with ridges 41 that define channels, as in FIG. 11, or with grooves 42, as in FIG. 12, or by a combination of both. When the interior surfaces of the chamber wall 40 are pressed upon the skin of the patient, or against one another, the channels or grooves admit the flow of liquid or air. As a result, the movement of liquid and air throughout the treatment space 14 and in and out of the chamber 12 is facilitated. The channels or grooves may be disposed as a pattern of short nubs or depressions 43 as seen in FIG. 13, as an irregular grid 44 as shown in FIG. 14, as a series of branches 45 as shown in FIG. 15, as a series of narrow bands 46 as shown in FIG. 16, or in other configurations achieving a similar result.

Figures 17, 18:
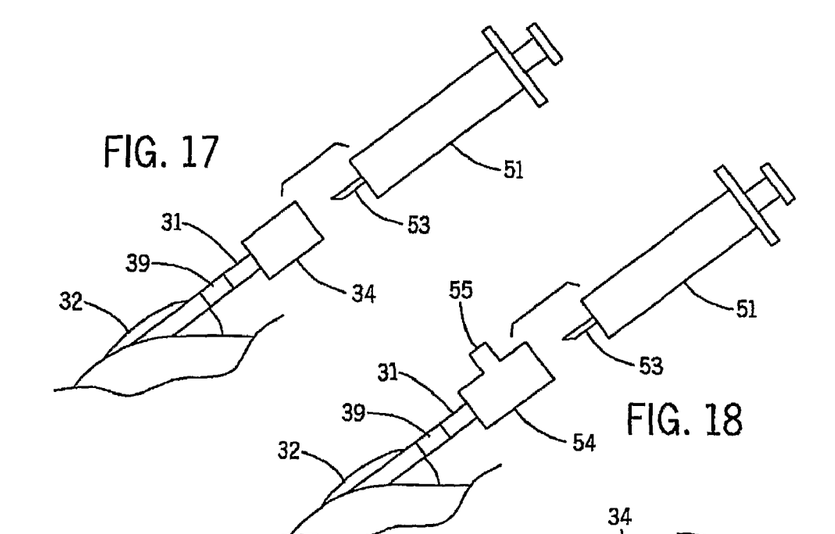
FIG. 17 is a perspective view of a portal with a valve fitted to the tube of a wound chamber.
FIG. 18 is a sectional view of a portal with a valve for exhausting air withdrawn from the interior of a wound chamber.

Turning now to FIGS. 17 and 18, a delivery/extraction device 51, such as a syringe, may be engaged with the portal 34 to allow delivery of treatment fluid and/or treatment additives to the treatment space 14 or removal of liquid or gases from the treatment space 14. For example, the delivery/extraction device 51 may include a fitting 53, such as a male Luer fitting, complementary to a female Luer fitting used as the portal 34. In the case of complementary female and male Luer fittings, the rotation of the male fitting 53 on the delivery/extraction device 51 opens a valve in the female portal 34 extending from the tube 31. The delivery/extraction device 51 may include devices other than the syringe illustrated. For example, the delivery/extraction device 51 may include a rigid or flexible container for holding one or more liquid or powdered treatment substances that may be delivered to the treatment space 14. Alternatively, fitting 34 may be constructed of a self-sealing material to accommodate a syringe having a hollow steel needle that is inserted through the self-sealing material to allow injection of fluids and/or withdrawal of wound fluid or air from the treatment space 14.

FIG. 18 shows a fitting 54 containing an exhaust valve 55. When this valve 55 is operational, the delivery/extraction device 51 can be operated to exhaust air from the chamber treatment space 14. After the desired amount of air has been exhausted, the valve 55 can be set to admit the flow of liquid from the delivery/extraction device 51 into the delivery tube 31. Other valves with various automatic, semi-automatic, and manual operations may be used to facilitate the extraction or introduction of air and liquid.

The length of the tube 31 may vary with the particular implementation. In an application where the tube 31 is provided to increase the distance between the delivery/extraction device 51 to protect the patient and/or chamber 12 from a needle, the tube 31 should be at least longer than the needle. In cases where the limb dressing 10 is intended to be covered with a secondary dressing, the tube 31 may be still longer. For example, the tube 31 may be between one inch and twenty-four inches in length. The tube 31 is generally flexible and may be foldable against itself depending on the specific implementation.

Figure 19:
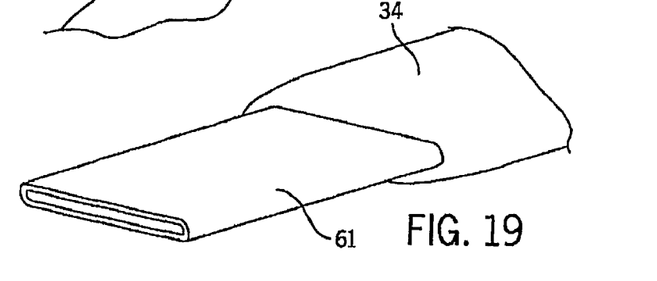
FIG. 19 is a perspective view of a collapsible tube that may be used with a wound chamber.
Figure 20:
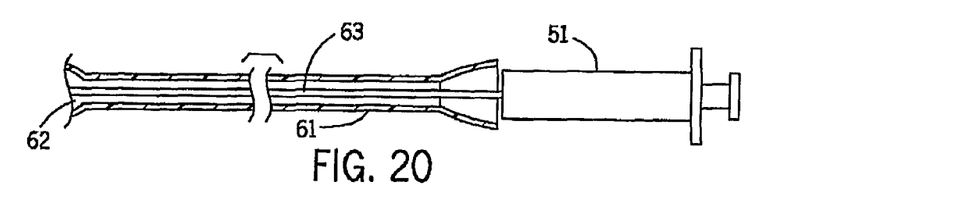
FIG. 20 is a perspective view of a syringe with a flexible delivery tip inserted into the collapsible tube of FIG. 19.

Referring to FIGS. 19 and 20, another embodiment is illustrated wherein the tube 31 of FIG. 1 is a collapsible tube 61 formed of a flexible, collapsible material that normally lies flat. The delivery/extraction device 51 may be a syringe with a flexible tip 63 that is inserted into the collapsible tube 61. The flexible tip 63 may be inserted throughout the entire length of the collapsible tube 61 such that it exits the collapsible tube 61 and extends directly into the treatment space 14. In some embodiments, e.g., where fluids are being added, the flexible tip 63 may be shorter than the collapsible tube 61. The collapsible tube 61 expands as necessary to allow the insertion of the flexible tip 63 and/or treatment fluids. When the flexible tip 63 is withdrawn, the collapsible tube 61 collapses and forms a watertight and airtight seal with respect to the treatment space 14. In some embodiments, the collapsible tube 61 may have a flared end 62 where it interfaces with the chamber 12, i.e., either terminating at the chamber 12 or extending into the chamber 12. The flexible tip 63 may be positioned within the flared end 62, yet not within the treatment space 14 to allow removal of fluids or air from the treatment space 14.

Figure 21:
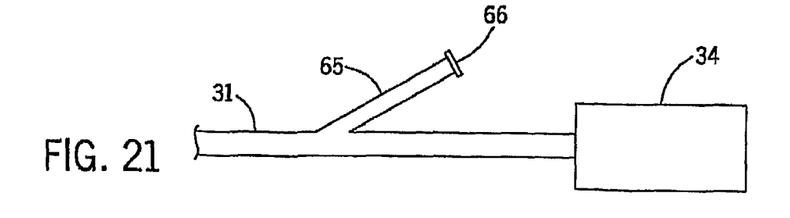
FIG. 21 is a perspective view of the delivery tube equipped with a fitting and an auxiliary port.

As seen in FIG. 21, the tube 31 may be equipped with a portal 34 that is a fitting, such as female Luer fitting, as well as an auxiliary portal 66, which may be made of self-sealing material for example, located on a branch tube 65. The availability of two portals 34 and 66 increases the flexibility of the limb dressing 10 by allowing users to employ needles or needleless delivery/extraction devices 51.

The tube 31 allows the portal 34 to be located a distance away from the limb 16, the wound 18, and the chamber 12. Hence, if treatment fluids are be introduced into the treatment space 14 using a needle, the likelihood of inadvertently contacting the patient or health care provider or breaching the chamber 12 is reduced. Also, if the limb dressing 10 is covered by a secondary dressing (not shown), the wound 18 may still be treated through the tube 31 without requiring removal of the secondary dressing.

The limb dressing 10 described above has numerous applications. The tube 31 may be used to introduce a wide variety of treatment fluids and/or additives. The limb dressing 10 allows monitoring of the wound 18, which is useful in enhancing the healing process. The chamber 12 allows visual monitoring of the wound 18 itself as well as the monitoring of fluid within the treatment space. This monitoring provides feedback to assist in the precise control of treatment variables and facilitates research. Fluid extracted from the system can be analyzed for factors that indicate wound healing status and also for the presence of deleterious factors such as microorganisms, low oxygen, high carbon dioxide and adverse pH. The fluid may be tested for the number and type of bacteria and other microorganisms per cc of fluid, the number and type of cells, the amount and type of proteins, and other factors. Clinical diagnosis of the wound physiology and the patient may also be conducted. Upon diagnosis, further treatment of the wound 18 may be commenced by introducing treatment additives and controlling treatment variables. Depending on the type of wound, the extracted fluid can be tested, e.g., for: (a) the presence of microorganisms, (b) cells, (c) amount and type of protein, (d) chemicals, (e) oxygen, (f) carbon dioxide levels, and/or (g) pH. This data may be recorded and used for wound diagnosis. Once diagnosis is complete, fluid treatment intervention may be adjusted accordingly.

Additional growth factors that are produced by the wound 18 may also be measured when extracted fluid is analyzed. Additional factors that may be tested for are the presence and the amounts of various inflammatory mediators and various antigens. The presence of antigens could serve an important diagnostic purpose and may be tested with specific antibodies that would be delivered through the wound chamber. This information is useful in deciding what to replace and how to treat, and would indicate improvement of the wound 18. The limb dressing 10 establishes an environment that allows the positive factors produced by the body to be present.

An exemplary, but not exhaustive, list of treatment materials includes anesthetics, antibiotics, chemotherapeutics, growth factors, cell culture media, cells, oxygen, buffering agents, enzymes, and immune modulators. The cells added may include cells that have been genetically modified prior to transplantation in the wound 18 or may include other gene therapy additives such as DNA, genes, genetic material, genetic vectors, etc.

The limb dressing 10 also allows control of the treatment environment within the treatment space 14. An exemplary, but not exhaustive, list of treatment variables includes temperature, colloid osmotic pressure, pH, ion concentration, glucose concentration, amino acid content, fat concentration, oxygen concentration, and carbon dioxide concentration.

By controlling treatment variables and by adding selected treatment additives, a variety of treatment techniques may be implemented. Those of ordinary skill in the art, in light of this disclosure, may identify numerous such treatment techniques, and the application of the present invention is not limited to any particular treatments. By way of illustration, a non-limiting sample of treatments that may be implemented in accordance with the present invention include cell treatment techniques, such as application of stem cells, gene therapy drugs, or cellular matrix gel suspension, infection treatment techniques, such as antibacterial or bacteriostatic treatments, or general treatment techniques, such as negative pressure therapy.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

The invention claimed is:

1. A wound dressing, comprising:
   a chamber defining a treatment space and at least one opening communicating with the treatment space;
   a tube having a first end coupled to the chamber, the tube communicating with the treatment space; and
   a plurality of channels defined on an inner wall of the chamber, the plurality of channels being in communication with the treatment space;
   wherein the channels are defined by a plurality of spaced-apart grooves forming a grid pattern.

2. A wound dressing as recited in claim 1 wherein the opening is sized to receive a limb of a patient.

3. A wound dressing as recited in claim 1, wherein the channels comprise at least one of ridges and grooves defined on the inner wall of the chamber.

4. A wound dressing as recited in claim 1, wherein the channels are arranged in at least one of a linear interrupted pattern, a grid pattern, a series of branches pattern, and a band pattern.

5. A wound dressing as recited in claim 1, further comprising a portal coupled to a second end of the tube.

6. A wound dressing as recited in claim 5, wherein the tube comprises a compressible tube, further comprising a delivery/extraction device including a flexible tip adapted to extend into the compressible tube through the portal.

7. A wound dressing as recited in claim 1, wherein a portion of the tube extending into the treatment space comprises a plurality of branches.

8. A wound dressing as recited in claim 1, further comprising a plurality of openings defined in the tube in a portion of the tube extending into the treatment space.

9. A wound dressing as recited in claim 1, wherein the chamber has an increased thickness in a region proximate a portion of the tube extending into the treatment space.

10. A wound dressing as recited in claim 1, further comprising a tab operable to reduce the cross-sectional area of the chamber.

11. A wound dressing as recited in claim 1, where the plurality of spaced-apart grooves form an irregular grid pattern in which at least some of the spaced-apart grooves face away from neighboring spaced-apart grooves.

12. A wound dressing as recited in claim 1, wherein the plurality of spaced-apart grooves are disposed at an acute angle relative to the opening.

13. A wound dressing, comprising:
    a chamber defining a treatment space and at least one opening communicating with the treatment space;
    a tube having a first end coupled to the chamber, the tube communicating with the treatment space; and
    a plurality of channels defined on an inner wall of the chamber by a plurality of spaced-apart ridges forming a grid pattern, the plurality of channels being in communication with the treatment space.

14. A wound dressing as recited in claim 13, where the plurality of spaced-apart ridges form an irregular grid pattern in which at least some of the spaced-apart ridges face away from neighboring spaced-apart ridges.

15. A wound dressing, comprising:
    a chamber defining a treatment space and at least one opening communicating with the treatment space;
    a tube having a first end coupled to the chamber, the tube communicating with the treatment space; and
    a plurality of at least one of spaced-apart protrusions and spaced-apart indentations defining a plurality of channels on an inner wall of the chamber, the plurality of channels being in communication with the treatment space and configured to direct fluids through the channels,
    wherein the at least one of spaced-apart protrusions and spaced-apart indentations form a grid pattern.

16. A wound dressing as recited in claim 15, wherein the at least one of spaced-apart protrusions and spaced-apart indentations are disposed at an acute angle relative to the opening.

* * * * *